United States Patent [19]

Schaeufele

[11] 4,320,147
[45] Mar. 16, 1982

[54] DISINFECTANT COMPOSITION AND THE USE THEREOF

[75] Inventor: Peter J. Schaeufele, Ringwood, N.J.

[73] Assignee: Lonza Inc., Fair Lawn, N.J.

[21] Appl. No.: 148,395

[22] Filed: May 9, 1980

[51] Int. Cl.$^3$ ............................................. A01N 33/12
[52] U.S. Cl. .................................................... 424/329
[58] Field of Search ........................................ 424/329

[56] References Cited

U.S. PATENT DOCUMENTS 3,836,669  9/1974  Dadekian ............................ 424/329

OTHER PUBLICATIONS

McCutcheon's Detergents and Emulsifiers, 1971 Annual, p. 87.
Lonza Formulation 70-12 (a formulation of Lonza Inc. of Fair Lawn, N.J.).

*Primary Examiner*—Allen J. Robinson
*Attorney, Agent, or Firm*—Bert J. Lewen

[57] ABSTRACT

A hospital-strength disinfectant cleaner having both organic soil tolerance and disinfectant hard water tolerance comprising as active ingredients alkyl dimethyl benzyl ammonium chloride and octyl decyl dimethyl ammonium chloride. The cleaner is an aqueous solution containing at least 800 ppm of the active ingredients and demonstrates disinfectant activity in water having a hardness of from 300 to 400 ppm.

6 Claims, No Drawings

DISINFECTANT COMPOSITION AND THE USE THEREOF

BACKGROUND OF THE INVENTION

It has long been desired to obtain a hospital-strength disinfectant cleaner having tolerance to both hard water and soil load. This objective has been elusive, especially for compositions having active ingredient concentrations in an economically useful range, and for killing the more highly resistant bacteria, such as *pseudomonas aeruginosa*. Blends of quaternary ammonium compounds have long been known in the art. Included among the known compositions are blends of alkyl dimethyl benzyl ammonium chlorides and octyl decyl dimethyl ammonium chlorides, known commercially as Lonza Formulation 70-12 (a formulation of Lonza Inc. of Fair Lawn, N.J. Such formulations were used in dilutions of about 500 ppm active ingredients and were not sold for or useful as broad-spectrum hospital-strength disinfectant cleaners for use in hard water, i.e., water having a hardness in the range of from 300 to 400 ppm.

BRIEF SUMMARY OF THE INVENTION

The subject invention relates to a germicidal composition comprising a total of at least 800 ppm of alkyl dimethyl benzyl ammonium chloride and octyl decyl dimethyl ammonium chloride and the use of such compositions as hospital-strength disinfectants in water having a hardness of from 300 to 400 ppm. Based on the total active ingredients, the compositions may contain from 20 to 80 wt. % of the alkyl dimethyl benzyl ammonium chloride, preferably from 30 to 50 wt. %.

DETAILED DESCRIPTION OF THE INVENTION

The alkyl dimethyl benzyl ammonium chloride compositions used in the invention contain long chain alkyl groups having from 12 to 16 carbon atoms. Most preferable are those compositions which contain a blend of long chain alkyl groups, particularly $C_{14}$, 50%; $C_{12}$, 40%; $C_{16}$, 10%. The octyl decyl dimethyl ammonium chloride compositions have a statistical distribution of approximately 25% dioctyl, 25% didecyl and 50% octyldecyl dimethyl ammonium chloride. Such compounds are described in U.S. Pat. No. 3,836,669.

While broader ranges may be used, as described above, the most preferred compositions contain, based on total weight of the active ingredient, 40% of the alkyl dimethyl benzyl ammonium chloride and 60% of the octyl decyl dimethyl ammonium chloride. When applied as a disinfectant in the presence of hard water, the total concentration of the active ingredients is at least 800 ppm., preferably from 800 to 1000 ppm, most desirably from 825 to 850 ppm.

The foregoing compositions provide superior germicidal and fungicidal activity far beyond that achieved with currently available quaternary ammonium compounds. They give better disinfectant performance at lower use concentrations; have a broad spectrum of biocidal activity against both gram-positive and gram-negative organisms; have greater hard water tolerance for sanitizing activity at lower use concentrations; give superior fungicidal performance; and have substantial organic soil tolerance in accordance with the latest Environmental Protection Administration requirements. Their hard water tolerance is not only sufficient for sanitizing performance but also for disinfection against the most resistant bacteria, such as *pseudomonas aeruginosa*. Most strikingly, when used in concentrations in excess of 800 ppm, the compositions of the invention demonstrate disinfectant activity even in the presence of water having hardnesses up to 400 ppm.

In addition to the foregoing, the compositions of the invention may also contain non-ionic surfactants such as linear primary and secondary alcohol polyglycol ethers (9 to 12 moles average ethylene oxide) or nonyl phenyl polyoxyethylene (9 to 13 moles average ethylene oxide). Additionally, builder salts such as tetrasodium ethylene diamine tetraacetate (EDTA), sodium metasilicate. $5H_2O$ and sodium sesquicarbonate may be added. The EDTA also functions as a chelating agent.

Generally, the active ingredients of the instant invention are prepared in the form of concentrates which are thereafter formulated for the end use desired. Examples of such concentrates are as follows:

| Chemical Composition | Concentrates | |
| --- | --- | --- |
|  | A | B |
| Active Ingredients | | |
| Alkyl ($C_{14}$, 50%; $C_{12}$, 40%; $C_{16}$, 10%) dimethyl benzyl ammonium chloride | 20.0% | 32.0% |
| Octyl decyl dimethyl ammonium chloride | 15.0% | 24.0% |
| Dioctyl dimethyl ammonium chloride | 7.5% | 12.0% |
| Didecyl dimethyl ammonium chloride | 7.5% | 12.0% |
| Inert Ingredients | 50.0% | 20.0% |
| Physical Properties | | |
| Average molecular weight | 342 | |
| pH (10% solution) | 7–8 | |
| Physical state | Liquid | |
| Color | Clear to light amber | |
| Flash point (Seta Flash) | 116° F. | 118° F. |
| Specific gravity at 25° C. | 0.946 | 0.912 |
|  | (7.89 lbs/gal) | (7.61 lbs/gal) |

Typical formulations for hospital-strength disinfecting cleaners which meet the current EPA organic soil contamination requirements (efficacy testing in the presence of 5% blood serum) and all AOAC use dilution testing (demonstrating disinfectant activity in the presence of water having 400 ppm hardness) are shown below:

| Formulation I | % wt/wt |
| --- | --- |
| Active Ingredients | |
| Concentrate A (50% active sol'n) | 21.7 |
| Tetrasodium ethylene diamine tetraacetate (38% active) | 7.0 |
| Sodium metasilicate . $5H_2O$ | 1.0 |
| Inert Ingredients | |
| Linear primary alcohol polyglycol ether (9–12 moles average ethylene oxide) | 4.5 |
| Water | 65.8 |

One ounce of the foregoing formulation is diluted in one gallon of water. This yields 848 ppm active quaternary ammonium compounds. This dilution passes the required AOAC use-dilution tests against *staphylococcus aureus* ATCC No. 6538; *salmonella choleraesuis* ATCC No. 10708; and *pseudomonas aeruginosa* ATCC No. 15442. Additionally, the dilution has outstanding sanitizing activities. The dilution has a pH of 11.1 when diluted in distilled water. The formulation has acceptable freeze-thaw stability and is stable when stored at 0° C., 20° C. and 40° C.

Another useful formulation for a hospital-institutional disinfecting cleaner is shown below:

| Formulation II | |
|---|---|
| | % wt/wt |
| Active Ingredients | |
| Concentrate A (50% active sol'n) | 11.0 |
| Tetrasodium ethylene diamine tetraacetate (38% active) | 5.0 |
| Sodium metasilicate . 5H$_2$O | 0.5 |
| Inert Ingredients | |
| Linear secondary alcohol polyglycol ether (9-12 moles average ethylene oxide) | 2.5 |
| Water | 81.0 |

Fragrance and dye may be added to the above formulation, but should naturally be tested for proper stability. The foregoing formulation, when diluted 2 oz. to the gallon, forms a dilution having 850 ppm active quaternary. The formulation was tested in accordance with EPA organic soil contamination requirements as a one-step disinfecting cleaner/sanitizer. All testing was performed in the presence of water of 400 ppm hardness to demonstrate disinfection. The dilution passes the above AOAC use dilution tests and also has outstanding sanitizing properties. The pH of the dilution in distilled water was 11.0. The freeze-thaw stability of the formulation was acceptable, as was the storage stability at 0° C., room temperature, and 40° C.

The foregoing disinfectant activity of the quaternary ammonium blends of the invention is indeed surprising and unexpected. Other similarly configured quaternary ammonium compounds, including blends thereof, cannot achieve this high disinfectant activity in the presence of hard water at these commercially useful concentrations. Similarly, compositions containing less than 800 ppm of the quarternary ammonium compound do not show disinfecting activity in the presence of hard water, particularly against the more resistant bacteria. In contrast to the compositions of the invention, the individual quaternary ammonium components would not be useful in water of a 400 ppm hardness, unless used in amounts exceeding 1300 ppm.

I claim:

1. A disinfectant composition useful in hard water which comprises an aqueous solution of from 800 to 1000 ppm of active ingredients, said active ingredients being from 20 to 80 wt. % of alkyl dimethyl benzyl ammonium chloride, wherein said alkyl chain has from 12 to 16 carbon atoms, and from 80 to 20 wt. % of a mixture of octyl decyl, dioctyl and didecyl dimethyl ammonium chloride.

2. The composition of claim 1 wherein the active ingredients comprise about 40% of said alkyl, dimethyl benzyl ammonium chloride and 60% of said mixture.

3. The composition of claim 1 wherein the alkyl chain of said alkyl dimethyl benzyl ammonium chloride is composed of 50% $C_{14}$, 40% $C_{12}$ and 10% $C_{16}$.

4. A process for killing bacteria which comprises treating said bacteria with a disinfecting composition comprising an aqueous solution of from 800 to 1000 ppm of active ingredients, said active ingredients being from 20 to 80 wt. % of alkyl dimethyl benzyl ammonium chloride, wherein said alkyl chain has from 12 to 16 carbon atoms, and from 80 to 20 wt. % of a mixture of octyl decyl, dioctyl and didecyl dimethyl ammonium chloride in the presence of water having a hardness of up to 400 ppm.

5. The process of claim 4 wherein the disinfecting composition contains, as active ingredients, 40% of the alkyl dimethyl benzyl ammonium chloride and 60% of said mixture.

6. The process of claim 4 wherein the alkyl dimethyl benzyl ammonium chloride contains 50% $C_{14}$, 40% $C_{12}$ and 10% $C_{16}$ in the alkyl group.

* * * * *